(12) United States Patent
Basic et al.

(10) Patent No.: US 7,074,437 B2
(45) Date of Patent: Jul. 11, 2006

(54) MINERAL-PROTEIN PREPARATIONS (MPP) AND NEUROPATHIES IN DIABETES

(76) Inventors: Robert Basic, Dubravica 30, Zagreb (HR) 10000; Mirko Hadzija, G. Tadino 18, Zagreb (HR) 10000; Boris Subotic, Zahradnikova 32, Zagreb (HR) 10020

( * ) Notice: Subject to any disclaimer, the term of this patent is extended or adjusted under 35 U.S.C. 154(b) by 0 days.

(21) Appl. No.: 10/482,875

(22) PCT Filed: Jul. 5, 2002

(86) PCT No.: PCT/HR02/00034

§ 371 (c)(1),
(2), (4) Date: Jan. 6, 2004

(87) PCT Pub. No.: WO03/013563

PCT Pub. Date: Feb. 20, 2003

(65) Prior Publication Data

US 2004/0175436 A1    Sep. 9, 2004

(30) Foreign Application Priority Data

Jul. 6, 2001    (HR) .......................... P 20010326 A

(51) Int. Cl.
*A61K 35/78*    (2006.01)

(52) U.S. Cl. ................. 424/725; 424/682; 424/195.16
(58) Field of Classification Search ................ 424/725
See application file for complete search history.

*Primary Examiner*—Susan Coe
*Assistant Examiner*—S B McCormick-Ewoldt
(74) *Attorney, Agent, or Firm*—Katten Muchin Roseman LLP

(57) ABSTRACT

The increased level of glucose in blood is the result of the destruction of β cells of the Islets of Langerhans by autoimmune process in insulin-dependent form of diabetes or a relative lack of insulin in insulin-dependent form of diabetes. Constantly present hyperglycemia in diabetes and a relative lack of insulin aid the development of the neuropathy as a late complication of diabetes. For that purpose, a technical problem was set before the inventor with the request of the reduction of glucose in blood, and stopping of the process of the development of the neuropathy as the consequence of the "long" duration of diabetes. Such a mineral-protein preparation was prepared by which glycemia was successfully regulated, but the process was also stopped by depositing of $Ca^+$ in nerve cells. Those early changes caused by diabetes were successfully stopped, so that the appearance of the neuropathy, as a late complication in diabetes, was postponed. The mineral-protein preparation showed a hypoglycemia effect and stopped the development and progressing of the diabetic neuropathy.

18 Claims, 14 Drawing Sheets

The schematic presentation of mutual linking of and $AlO_4$ tetrahedrons in the zeolite crystal grid.

Figure 1

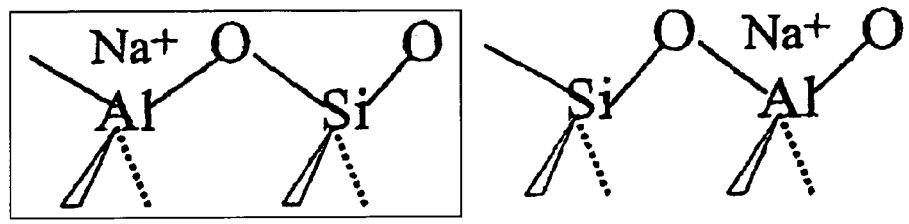

Figure 1. The schematic presentation of mutual linking of and $AlO_4$ tetrahedrons in the zeolite crystal grid.

Figure 2

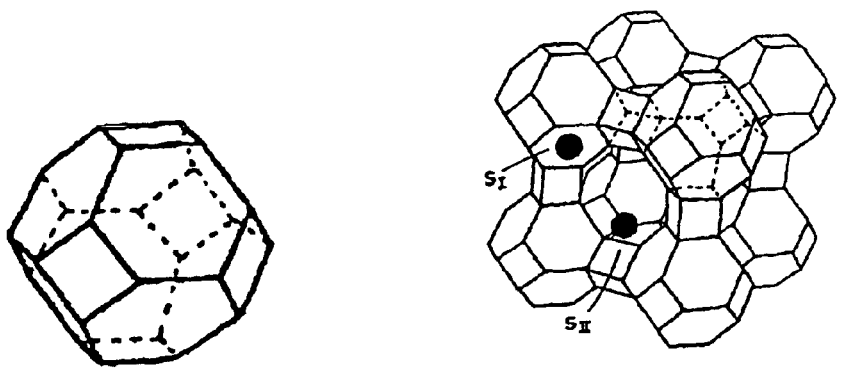

Figure 2. The schematic presentation of cut cubo-octahedron (sodalite unit) as a tertiary unit of the zeolite A structure (left) and the structure of the unit cell of the zeolite A (right). Atoms of aluminum and silicium are placed at intersections of edges, i.e. on the apexes of the cubo-octabedrons, while the oxygen atoms are between them, at the bisection of edges. S, and S,, represent positions of hydrated $Na^5$ ions in the structure of the zeolite A.

Figure 3

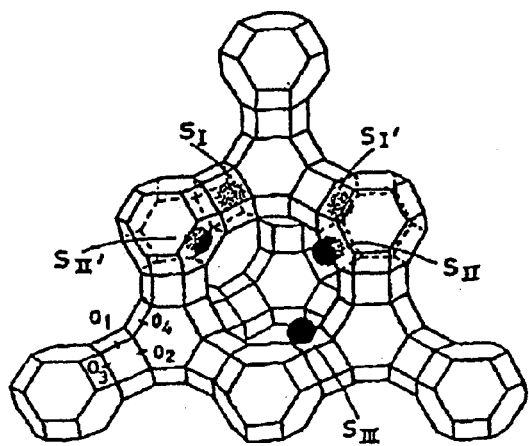

Figure 3. The schematic presentation of X and Y zeolites (faujasites) with the bolonging $S_I$, sit, $S_I$, $S_{II}$, and SU) positions. Atoms of aluminum and silicium are placed at intersections of edges, i.e. on the apexes of the cubo-octahedrons, while the oxygen atoms are between them, at the bisection of edges. The difference between the X and Y zeolites is manifested in the direction of Si/Al, silicium and aluminum atoms (Si/Al = 1-2 in the X zeolite; Si/Al = 1.5-3 in the Y zeolite)

a　　　　　　　　　　b　　　　　　　　　　　　c

Figure 4. (a) 5-1 secondary unit of the mordenite structure. (b) Projection of the cross-section of the crystal grid of mordenite along the axis of main channels. (c) The schematic presentation of the crystal grid of tnordenite.

Figure 5

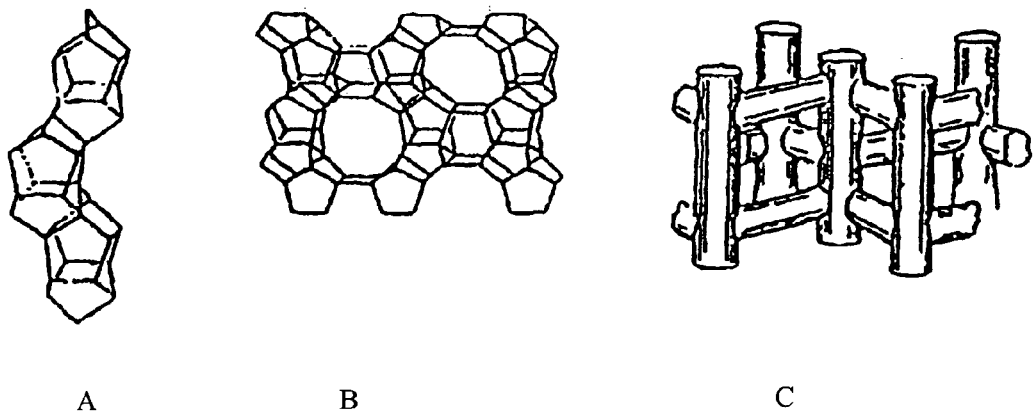

A  B  C

Figure 5. (a)' The characteristic chain structure composed of 5-1 secondary unit of the structure. (b) The crystal face (100) of a unit lattice of the ZSM-5 zeolite and silicalite. 10-member rings represent openings of sinusoidal channels parallel (001) with crystal faces of the ZSM-S zeolite and silicaiite. (c) The schematic presentation of structural channels in the ZSM-5 zeolite (Si/Al - 20-200) and silicalite (Si/Al - 20-200) and the silicalite (SilAl = oo).

Figure 6. The curve of the assimilation of glucose in diabetic CBA mice which were receiving the mineral part of MPP Figure 7. The curve of the assimilation of glucose in diabetic NOD mice which were receiving the mineral part of MPP Figure 8. The concentration of glucose in the blood of control diaetic mice (1) and diabetic mice treated with MPP (Working Example 16)

Figure 9

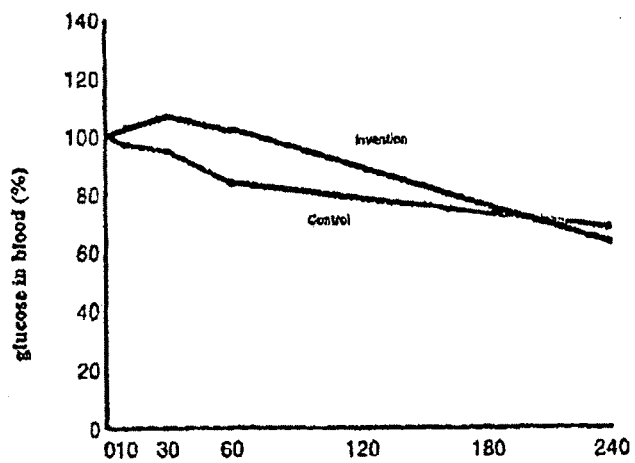

Figure 9. The concentration of glucose in the blood of diabetic CBA mice non-treated with MPP (Control) and treated with MPP (Working Example 17).

In diabetic mice which were receiving the MPP during 14 days (according to Working Example 17), the concentration of glucose in blood during four hours after introducing of the MPP was not changing in relation to control values (Figure 9).

Figure 10: Quantity of water drunk during 6 days of application of MPP (3 mice per group).

Figure 11. The volume of excreted urine in diabetic mice which were receiving MPP (3 mice per group) or 6 days.

Figure 12. The concentration of fructosamine in the serum of control (Control), diabetic (Diab. Groups), and diabetic mice treated with MPP (Diab.T) according to the Working Example 16)

Figure 13: The catalytic concentration of GST in the group of healthy, control and diabetic CBA mice treated ;with MPP (Diab. + MPP) (According to the Working Example 16)

Figure 14. Cross-section through n. *ischiadicus* of diabetic mice after 180 days of the duration of the disease.

Figure 15. Cross-section through n. *ischiadicus* of diabetic mice treated with MPP afte 180days of the duration of the disease.

MINERAL-PROTEIN PREPARATIONS (MPP) AND NEUROPATHIES IN DIABETES

FIELD TO WHICH INVENTION REFERS

This invention refers to the preparation consisting from synthetic zeolites and selected herbal proteins (MPP) which is applied for prevention of the development of neuropathies in persons suffering from diabetes. The present MPP stops the process of apoptosis caused by accumulation of $Ca^{2+}$ ions in cytoplasm of nerve cells.

INVENTION

The technical which was set before the inventor, and the solution of which is presented in this patent application, consists from the MPP which is applied for prevention of the development of neuropathies in patients suffering from diabetes, which will have the following characteristics that:
1) it contains plant proteins,
2) it reduces the concentration of glucose,
3) it can stop the process of depositing of $Ca^{2+}$ ions into nerve cells,
4) it stops the process of apoptosis in nerve cells stimulated by depositing of $Ca^{2+}$ ions,
5) the process of phagocytosis of apoptotic bodies is absent,
6) it stops the process of creating immunoglobulin on myelin fibres of the nerve membrane,
7) it reduces the depositing of immunoglobulin on nerve fibres,
8) it reduces the immunological destruction of nerve fibres mediated by the complement,
9) the pain caused by diabetic neuropathy is absent,
10) it contains substances for elimination of heart troubles,
11) it contains substances for elimination of digestive troubles,
12) it contains substances for elimination of free radicals,
13) it contains the daily dose of B complex vitamins,
14) it has a pronounced capability of ionic exchange,
15) it does not pass through villi,
16) it has a pronounced ionic exchange through the intestine-blood barrier,
17) its particles are of micron and submicron size,
18) it is chemically treated,
19) it reduces the concentration of $Na^+$ ions,
20) it is enriched with $Ca^{2+}$ ions,
21) the dose is reduced in relation to the natural zeolite,
22) it is suitable for oral administration,
23) no noticeable harmful side effects appear even with large daily doses, and in case of a long-term use,
24) it is not toxic,

INVENTION BACKGROUND

Diabetes mellitus is a syndrome of disturbed metabolism of glucose which arises due to hyperglycemia which is responsible for the majority of symptoms. Insulin is actually the key regulator of the metabolism of hydrocarbons, proteins and lipids, and a relative or absolute shortage of insulin effects the complete intermedial metabolism. It is supposed that biochemical disturbances are primarily determined by the amount of the insulin deficiency.

Diabetes of Type I, i.e. IDDM (Insulin Dependent Diabetes Mellitus) is characterized by progressive autoimmune process of the destruction of β cells of Islets of Langerhans by T lymphocytes (Eisenbarth, G S. New Engl. J. Med. 314:1360–1368, 1986). More precisely, IDDM is the result of the destruction of beta cells mediated by CD4+ and CD8+ cells and the function of antigen presenting cells (APC) (Frque F., Hadžija M., et al., Proc. Natl. Acad. Sci., USA, 91:3936–3940, 1994).

NOD (non-obese diabetic) mice develop the classical picture of diabetes which is completely identical to IDDM in people (Makino S., et al., Expl. Anim. 29: 1 (1980)). Furthermore, chemical diabetes caused by Alloxan in mice also develops the picture of diabetes with all the accompanying symptoms identical to the human form of diabetes of Type I (Dunn J. S., et al., Lancet II: 384–387, 1943).

The purpose of the therapy of diabetes is the normalization of the following parameters; the concentration of glucose in blood, the concentration of lipids, and the absence of glucose and acetone in urine.

In the therapy of diabetes, two principles of treatment are applied: firstly, the general one, and secondly, special principles of treatment of diabetes.

General Principles of Treating Diabetes

By treating diabetes, it is endeavored to achieve the state of normoglycemia and thus prevent the development of later complications. The general principles of treatment comprise, regardless of the type of diabetes: diet, physical activity, education and self-control. The nourishment must be composed so that it meets the daily needs for nutrient according to the age, sex, activities, height and weight. It is recommended that the diet consists of: 15–20% of proteins, 25–30% of fats, and 55–605 of hydrocarbons. The total daily quantity of substances must be divided into a larger number of smaller meals (5–6 during the day) in order that no major oscillations in the concentration of glucose in the blood would occur, the physical activity is important because it increases the exploitability of glucose in peripheral tissues with a proportionally reduced use of insulin. Education and self-control are important for understanding of the very disturbance, and for the daily self-control of the concentration of glucose in the blood.

Special Principles of Treating Diabetes

Treatment by exogenous insulin is applied in case of Type I Diabetes, where over 805 of the mass of the endocrinous part of the pancreas. The successfulness is high since, before the discovery of insulin, such persons used to die after 1.5 years, and today they live for even 50 years after the appearance of the disease.

Oral antidiabetics are not a replacement for insulin, but a support to the secretion of endogenous insulin or its hypoglycemic effect. Persons with the Type II Diabetes should take oral antidiabetics only in case if the correct nourishment and the corresponding physical activity have not given the desired results. Although the transplantation of pancreas, i.e. Islets of Langerhans, is one of the special principles of treatment of Type I Diabetes, it is still being researched today. Namely, the success of the transplantation depends on the number of transplanted islets, by which the isolation is still a problem, as well as the immunological reaction of rejection due to which various immunosuppressive must be used on a daily basis.

Metabolic Effects of Insulin

Insulin is a protein, with the molecular mass of 5734 Da. It consists of "A" and "B" chain, which are connected by two disulfide bridges, while the third disulfide bridge is within the "A" chain. "A" chain consists of 21 amino acids, and the "B" chain of 30 amino acids.

Insulin is synthesized by β cells of the Islets of Langerhans of the pancreas. The basic physiological function of insulin consists in maintaining of normoglycemia. Thus, insulin effects the metabolism of hydrocarbons so that it firstly suppresses the creation of glucose in the liver, and that happens if the concentration of insulin in the circulation ≈30 mU/L, and secondly so that it stimulates entering of glucose into peripheral tissues (by speeding up the translocation of the glucose transporter GLUT-4 on the surface of cells of skeletal muscles and of adipose tissue, and by activation of intracellular enzymes such as, e.g. glycogen synthetase). That happens if the concentration of insulin in the circulation ≈100 mU/L, which is usually present in the blood after a meal. Insulin is also a very potent inhibitor of lipolysis, and thereby also of the ketogenesis. The antilipolitic effect of insulin is manifested already at the insulin concentration of ≈10 mU/L. Insulin also inhibits the proteolysis, if its concentration in the blood is between 10–30 mU/L.

By binding of insulin to the extracellular α-subunit of receptor, the insulin-receptor complex activates the $Zn^{2+}$ dependent protein tyrosine kinase which makes the transmembrane β-subunit of insulin receptor and, due to that, autophosphorylation of receptor and other proteins with phosphate groups over ATP (Reddy and Kahn, 1988) arises. The activation of phosphatidylinositol-specific phospholipase C leads towards the hydrolysis of membrane phosphoinositides. Thus, the cyclic inositol-phosphate glucosamine arises, the second messenger which activates phosphodiesterases, reduces the content of the intracellular cAMP and produces diacylglycerol which activates protein kinase C (Saltiel, 1986). Protein kinase C regulates numerous enzymes and the very insulin receptor through phosphorylation (Van de Werve, 1985).

During testing of Type I Diabetes by insulin, the slow absorption of insulin from the subcutaneous tissue results in its inadequate pique at the time of the meal and after taking it with hyperglycemia between two meals (due to a low concentration of insulin in the port vein). Insulin deficiency leads to an increased release of glucose by the liver, and that is the reason of hyperglycemia on an empty stomach, i.e. of postprandial hyperglycemia. The consequence of the low concentration of insulin includes the increase of the secretions of glucagon from α-cells of the Islets of Langerhans of the pancreas.

Insulin resistance is often joined with the appearance of obesity, the intolerance of glucose, hypertension, dyslipidemy, disturbances in blood coagulation and the speeded up aterogenesis and it is also referred to as the Syndrome X.

Role of Plant Proteins in Treatment of Diabetes

The results of sequencing of the human genome just published stimulate researches about the role of small target molecules and proteins connected with diseases (Engl. target).

The completed sequencing of the human genome revealed a number of "harmful" genes on all chromosomes. Those results indicate and reveal a number of target places for medicines. In that context, a new strategy of research for obtaining of new medicines is started. That strategy first comprises target places (primarily, those are proteins, but that also includes parts of nucleic acids), and secondly, the ligand, i.e. proteins of small molecules as a substitute to the "ill" target place.

Plants contain four main types of molecules: hydrocarbons, proteins, nucleic acids and lipids. Beside the stated ones, plants contain other types of molecules in smaller quantities, e.g.: alkaloids, terpenoids, phenols, sterols another so-called "secondary metabolites".

Hydrocarbons in plants include monomers called monosaccharides and polymers called polysaccharides. Polysaccharides which are included in the construction of the plant cells are called structural polysaccharides. The best known structural polysaccharide in plants is cellulose (it makes 40%–60% of the cell wall). Reserve polysaccharides serve as the reserve of food, and the best known in plants are starch and insulin.

After cellulose, proteins make the largest remaining part of the biomass of the living plant cell. Proteins in plant cells are made of 20 various amino acids bound into polypeptides. As well as in case of hydrocarbons, proteins also have an important role in the construction of the cell (structural proteins), and they also serve as a reserve. Unlike hydrocarbons, proteins can also be enzymes. Structural proteins of the cell wall are called extensions and have an important role in its expansion during the very growth of the plant. Extensions are proteins rich in hydroxyproline, serin, threonine and the asparaginic acid. Plant cells contain various kinds of membranes, each has a different protein system. E.g. the inner membrane of mitochondrions and chloroplasts contains about 75% of proteins while the membrane which surrounds the plant cell has about 50% of proteins. The majority of the non-protein part of the membrane which surrounds the plant cell is made by lipids. The reserve proteins in plants are most often present in seeds and they serve as the source of nutrients during germination. The contents of proteins in seeds depends on the plant species. Some reserve proteins of plants are: zein, gliadin, ricin D, abrin, etc. Many plant proteins have the function of enzymes and catalyze biochemical reactions. One example is α-amylase, the enzyme which disintegrates amylose.

Plant Peptides and Amino Acids

In 1981, Khanna et al. published the results of the research about isolation of "polypeptides p" from the fruit and seeds of the plant *Moomordica charantia* L. (Cucurbitaceae). "Polypetide p" consists of 17 various amino acids and has the molecular mass of 11,000. When the s.c. is applied in rodents, primates and people, its insulinomymetic effect in the dose of 0.5 units/kg (1.8 mg/ml=40 units) is noticed. Sulfoxide amino acids: s-methylcysteine sulfoxide (SMCS) and S-allylcystein sulfoxide (SACS) isolated from plants *Allium cepa* L. and *Allium sativum* L. have caused the loss of body mass and the content of glycogen in liver after a month of per oral application in rats with experimentally induced diabetes (Sheela et al., 1995).

In 1998, Sauvaire et al. have isolated, and in 1999, Broca et al. have described the in vivo effect of 4-hydroxyisoleucine as a new stimulator of the insulin secretion from the seeds of *Trigonella foenum graccum* L, 4-hydroxyisoleucine aids the glucose induced secretion of insulin both on the model of isolated Islets of Langerhans, and in people. Its stimulating effect in a dose of 100 μmol/L to 1 mol/L was dependent exclusively on the stimulation of the secretion of insulin by glucose, i.e. it did not show the activity in case of low concentrations of glucose (3 mmol/L) or the basal concentration of glucose (5 mmol/L).

The fruit of the plant *Blighia sapida Koenig* (Sapindaceae) contains emetic ingredients: hypoglycine A and its γ-L-glutamyl dipeptide, hypoglycine B, which indicate a hypoglycemic activity, they act in such a way that they inhibit oxidation of long-chain fatty acids. Hypoglycine A is twice stronger hypoglycemic compound than hypoglycine B which is also a teratogen, and thus too toxic for therapeutic use (Tanaka et al., 1972; Oliver-Bever and Zahnd 1979).

Development of Neuropathy in Diabetes

Neuropathy is a common late complication of diabetes which affects somatic and autonomic peripheral nerves. Neuropathy occurs in a certain percentage in Type I and Type II Diabetes (Greene, D A, et al., Diabetes Care. 15:1902–6, 1992). Peripheral nerve abnormalities in people and in the animal model of diabetes are manifested as the decreased conductibility of nerves, axonal reduction, and nerve fiber loss (Behse F F, et al., J. Neurol. Neurosurg. Psych. 40:1072–82, 1977; Brismar. T. Metab. Clin. Exp. 32:112117, 1983; Sima, A A F, et al., Ann. Neurol. 18:21–29, 1985), in connection with metabolic alterations (Green, D A, et al., Diabetes 37:688–693, 1988), including altered calcium signaling (Levy, J, et al., Am. J. Med. 96:260–273, 1994). Existing studies indicate that altered homeostasis of calcium ions is a widespread occurrence in IDDM and NIDDM. Both, in people suffering from diabetes, and in animal models of diabetes, the identical change was observed, which is the increase of the Ca2+ ions in the cytosol (Hall, K E, et al., J. Physiol. 486:313–322, 1995; Nobe, S, et al., Cardiovas. Res. 24:381, 1994.; White, R E, J. Pharmacol. Exp. Ther. 253:1057–1062, 1993.; Kappelle, A C, et al., Br. J. Pharmacol 111:887–893, 1992). The increase of the concentration of calcium ions aids the process of natural atrophy (apoptosis) of nerve cells, but that process has been shown in a number of other experimental models as well (Trump, B F, et al., FASEB J. 9:219–228, 1995; Down, D., Phosphoprotein Res. 30:255–280, 1995; Joseph, R, et al., Mol. Brain. Res. 17:70–76,1993).

The latest researches suggest that "serum factors" have an important role in the pathogensis of diabetic neuropathy in patients with Type I diabetes mellitus. By incubation of β-cells of the Islets of Langerhans in conditions of the general tissue culture, when the serum of patients with Type I or Type II Diabetes was added to the medium (Hadžija, M, et al. Period. Bio 1.97:313–317, 1995), apoptosis in β-cells of the Islets of Langerhans is connected with the increase of the concentration of L-type calcium ions (Juntti-Berggren, L, Science 261:86–89, 1993). It was also shown that neuroblastoma cells demonstrated a reduced growth, the increase of entering of $Ca^{2+}$ ions, i.e. the intensified apoptosis if they were exposed to the serum of patients suffering from Type I Diabetes with neuropathies (Pittinger, G L, et al., Diabetic. Med. 10:925–932, 1993; Pittinger, G L, et al., Diabetic Med. 12:380–386, 1995: Pittinger, G L, et al., J. Neuroimmunol. 76:153–160, 1997; Migdalis, I N, et al., Diabetes. Res. Clin. Pract. 49:113–118, 2000). The complement-independent, $Ca^{2+}$-dependent inductions of apoptosis of nerve cells aid the appearance of autoimmune immunoglobulins in diabetes on nerve fibres (Srinivasan, S M, J. Clin. Invest. 102:1454–1468, 1998).

the characteristics of zeolites, such as the possibility of ionic exchange, existence of in intercrystalline pores which let through molecules of various dimensions, the existence of strong acidic places and places active for the reactions catalyzed by metals, etc. make them very interesting for a wide industrial implementation, as well as for fundamental researches (Flanigen, E. M. in: Proc. Fifth. Int. Conf. Zeolites (Ed. L. V. C. Rees), Heydon, London-Philadelphia-Rheine, 1980, p. 760; Vaughan D. E. W., Chem. Eng. Prog., 25, 1988; Cornier, J., Popa, J. M., Gubelman, M, L'actualite, 405, 1992; Subotić, B., Bronić, J., Čižmek, A., Antonić, T., Kosanović, C., Kem. Ind. 43:475, 1994). The interest for using zeolites as catalysts, absorbents and means for softening of water in detergents has largely increased in the last three decades (Cornier, J., Popa, J. M., Gubelman, M., L'actualite, 405). There are annually millions of tons of zeolites used in the production of washing means (Cornier, J., Popa, J. M., Gubelman, M., L'actualite, 405), hundreds of thousands of tons in oil processing and in the petrochemical industry (Naber, J. E., de Jong, K. P., Stork, W. H. J., Kuipers, H. P. C. E, Post, M. F. M., Stud. Surf. Sci. Catal., 84C:2197, 1994), and the use in other fields is increasing too (Flanigen, E. N. in: Proc. Fifth. Int. Conf. Zeolites (Ed. L. V. C. Rees), Heyden, London-Philadelphia-Rheine, 1980, p. 760; Waughan, D. E. W., Chem. Eng. Prog., 25, 1988; Cornier, J., Popa, J. M., Gubelman, M., L'actualite, 405, 1992; Naber, J. E., de Jong, K. P., Stork, W. H. J., Kuipers, H. P. C. E, Post, M. F. M., Stud. Surf. Sci. Catal., 84C:2197, 1994.; Breck, D. W. in: The properties and Application of Zeolites, Special Publication (Ed. R. P. Towsand), 33:391, 1980.; Vaughan, D. E. W. in The properties and Application of Zeolites, Special Publication (Ed. R. P. Towsand), 33:294, 1980.; Flanigen, E. M., Pure Appl. Chem., 52:2191, 1980.), including the use of zeolites in medicine, agriculture and cattle breeding (Ramos, A. J., Hernandez, E., Animal Feed Sci. Technol., 65:197, 1997; Eriksson, H., Biotechnology Techniques 12:329, 1998.; Mumpton, F. A., J. Nat. Acad. Sci., 96:3463, 1999.).

Zeolites or molecular sieves are hydrated natural and synthetic aluminosilicate compounds with a unique spatial-network structure consisting of $SiO_4$ and $AlO_4$ tetrahedrons linked through common oxygen atoms (Breck, D. W., J. Chem. Educ. 41:678, 1964), as it is schematically presented in FIG. 1.

The negative charge of the aluminosilicate structure is caused by an isomorphic replacement of the silicium with the valence of four by aluminum with the valence of three is neutralized by hydrated cation ($Na^+$, $K^+$, $Ca^{2+}$, $Mg^{2+}$ etc.). In reality, $SiO_4$ and $AlO_4$ do not create single-dimensional chain structures in the structure of zeolites, as it is simplified in FIG. 1, but they create two-dimensional and three-dimensional basic structural units, the combination of which gives rise to three-dimensional spatial-network structures characteristic for zeolites (FIGS. 2–5). The specific structure of zeolite, unique, both in the relation with other aluminosilicates, and in relation to other crystal materials, is reflected in existence of structural cavities mutually linked by channels of a certain form and size (FIGS. 2–5). However, unlike other porous materials characterized by a specified arrangement of pores which are statistically distributed in various directions, the form and size of cavities and channels, as well as their mutual relationships are constant and exactly defined as structural parameters of a specific type of zeolites (Barrer, R. M., Zeolites and Clay Minerals as Sorbents and Molecular Sieves, Academic Press, London, 1978, p. 23), as can be seen in the stated examples of the structure of a unit lattice of the zeolite A (FIG. 2), faujasites (X and Y zeolites, FIG. 3), mordenite (FIG. 4) and the ZSM-5 zeolite and silicalite (FIG. 5).

The chemical composition of zeolites is usually presented by a general formula in the oxide form:

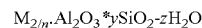

$$M_{2/n} \cdot Al_2O_3 \cdot ySiO_2 \cdot zH_2O$$

Where n is the charge number of cations M, while $y \geq 2$ and z depend on the type of the zeolite. The "zeolite" water results from hydration membranes of the compensation M cations. Therefore, the value z depends on the type of the M compensation cations, the number of M cations in a unit zeolite lattice and the level of M cations hydration in the zeolite lattice. By heating of the zeolite up to approx. 600° C., the "zeolite" water can be removed from the zeolite without the change of the structure. By cooling to the room temperature, the same quantity of water is bound to the zeolite, i.e. the processes of desorption and adsorption of zeolite water are strictly reversible.

In touch with electrolyte solutions, cations from a zeolite (Breck, D. W., J. Chem. Educ., 41:678, 1964; Fedorov, V. A., Tolmachev, A. M., Panchenkov, G. M., Zh. Fiz. Khim, 38:1248, 1964; Wolf, F., Foertig, H., Kolloid Z.-Z. Polymere, 206:48, 1965, Sherry, H. S., Adv. Chem. Ser., 101:350, 1971, Brooke, N. M., Rees, L. V. C., Adv. Chem. Ser, 101:405, 1971:Barrer, R. M., Klinowski, J., Phil. Trans 285:637, 1977). In the conditions of balance, the following applies: (Schwuger, M. J., Smolka, H. G, Tenside Detergents, 13:305, 1976):

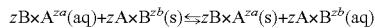

where zA and zB are charge numbers ("valences") of replaceable cations A and B, while aq and s denote the solution, i.e., the firm phase (zeolite).

Natural zeolites are impurified with various admixtures, therefore we used a synthetic zeolite with strictly defined characteristics in the preparation of this invention.

BRIEF DESCRIPTION OF THE DRAWINGS

FIG. 1 is a schematic presentation of mutual linking of and $AlO_4$ tetrahedrons in the zeolite crystal grid.

FIG. 2 is a schematic presentation of cut cubo-octahedron (sodalite unit) as a tertiary unit of the zeolite A structure (left) and the structure of the unit cell of the zeolite A (right).

FIG. 3 is a schematic presentation of X and Y zeolites (faujasites) with the bolonging S, sit, $S_r$, $S_{r1}$- and SU positions of the Zeolite.

FIG. 5 depicts (a) the characteristic chain structure composed of 5-1 secondary unit of the structure. (b) the crystal face (100) of a unit lattice of the ZSM-5 zeolite and silicalite. 10-member rings represent openings of sinusoidal channels parallel (001) with crystal faces of the ZSM-S zeolite and silicalite, and (c) the schematic presentation of structural channels in the ZSM-5 zeolite (Si/Al—20-200) and silicalite (Si/Al—20-200) and the silicalite (SilAl=oo).

FIG. 9 is a chart showing the concentration of glucose in the blood of diabetic CBA mice non-treated with MPP (Control) and treated with MPP (Working Example 17).

DETAILED DESCRIPTION OF THE INVENTION

Auxiliary Substances

Figure 4:
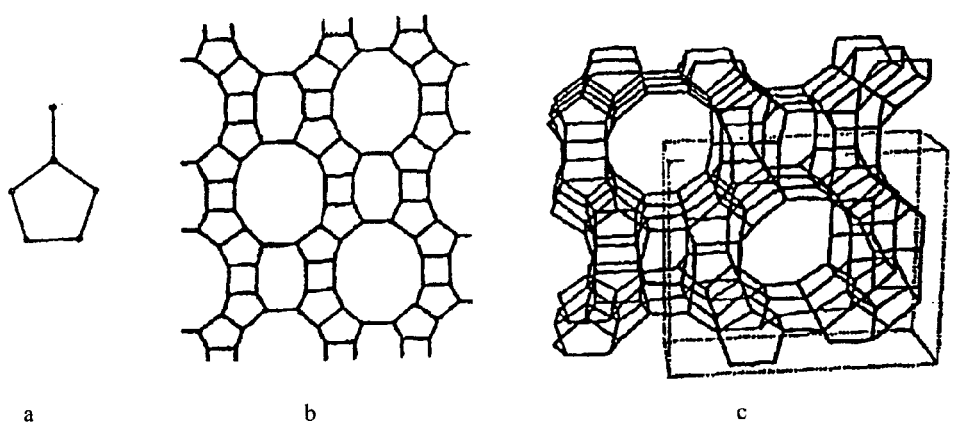
FIG. 4 depicts (a) 5-1 secondary unit of the mordenite structure, (b) projection of the cross-section of the crystal grid of mordenite along the axis of main channels, and (c) the schematic presentation of the crystal grid of mordenite.

In the production of pills and capsules, beside the MPP which is the subject of this invention, usual auxiliary substances are used, which are the carriers of certain functions:

Supplementing substances, e.g., preferably, lactose, microcrystalline cellulose, sorbitol, manitol, starch, etc.

Binding substances, e.g., preferably gelatin, cellulose, polyvinylpyrrolydon, methyl cellulose, etc.

Decomposition substances, e.g., preferably starch natrium-hydroxymethyl starch, microcrystalline cellulose, etc.

Sliding substances, e.g., preferably Mg-stearate, talc, stearine acid, hydrated plant oils.

The production of pills and capsules is carried out by the dry procedure.

Characterization of Calcium Form of Synthetic Zeolite (Ca-zeolite (S))

The calcium form of the synthetic zeolite Ca-zeolite (S) which appears in the form of fine white powder is characterized by methods of the x-ray diffraction, infrared spectroscopy, examination electronic microscopy, differential thermogravimetry and the distribution of the size of particles.

WORKING EXAMPLE 1

X-ray Diffraction Analysis

X-ray diffractograms of the Ca-zeolite (S) were obtained by the Philips' diffractometer with CuKα radiation within the field of Bragg angles 2Ө=10°-46° have shown that all the analyzed samples were 95–100% crystalline and without admixtures of other non-zeolite crystalline phases.

WORKING EXAMPLE 2

Infrared Spectroscopic Analysis

Infrared spectres of the Ca-zeolite (S) were recorded by the technique of the KBr pastille on the Perkin-Elmer infrared spectrometer System 2000 FT-IR, which showed that all the samples had spectres characteristic for zeolites, without admixtures of other non-zeolite crystalline phases.

WORKING EXAMPLE 3

Simultaneous Thermic Analysis

The simultaneous thermic analysis of the Ca-zeolite (S) was performed by the device TA 4000 System (Mettler-toledo), the speed of warming up in the atmosphere of nitrogen was 10 K/min. The results of the analysis have shown that the analyzed samples contain 12.5–22.6% of $H_2O$.

WORKING EXAMPLE 4

Measuring of Particle Size

Distributions of the sizes of particles of the Ca-zeolite (S) were measured by the method of dynamic scattering of the laser light by the device Mastersize X (Malvern). The results of the analyses have shown that the size of particles of the analyzed samples amounts to 0.5–20 micrometers.

WORKING EXAMPLE 5

Chemical Analysis

The chemical analysis of the Ca-zeolite (S) was carried out in the following way: Certain quantities of the zeolite were dissolved in the diluted solution of nitric acid. The solutions obtained in that way were diluted with distilled water up to levels suitable for measuring of sodium, aluminum and silicium concentrations by the method of atomic absorption spectroscopy (AAS). The acid stable zeolites were melted with the mixture of sodium carbonate and sodium tetraborate. The melt was dissolved in the diluted solution of HCl and diluted with distilled water up to the level suitable for measuring of the sodium, aluminum and silicium concentrations by the AAS method.

The concentrations of sodium, aluminum and silicium in the stated solutions were measured by the atomic absorption spectrophotometer 3030B (Perkin-Elmer). The results of the chemical analysis have showed that the analyzed samples contain 6.5–15.6% of CaO, 11.8–28.4% of $Al_2O_3$, 33.5–69.3% $SiO_2$.

Preparation of Oligopeptides

WORKING EXAMPLE 6

Isolation of Proteins of Nettle Root, Stalk and Leaf

Urticae Radix, Herba Et Flos

*Urtica Dioica* L., Urticaceae-Nettle-Nettle

From 1 kg of root, stalk and leaf, cut into tiny pieces, an alcoholic extraction was made through 5 days. By cold distillation, alcohol was removed from the extraction. By further procedure, oligopeptides of nettle were froze and lyophilized. In order to remove impurities contained by the plant extract, lyophilized nettle extract was applied on the column Sephadex G-25. Protein components were eluted from the column by the use of Tris-HCl buffer as the fraction 12. The absorption of protein was measured at 280 nm. Collected fractions from 1 ml each were submitted to the dialysis and lyophilized. The qualitative system of amino acids was determined on a thin layer of cellulose (Merck), in the mixture of the solvent: n-butanol:acetone acetic acid:water,

WORKING EXAMPLE 7

Isolation of Proteins of Milk Vetch Root

Astragali Radix

*Astragalus Membranaceus* (Fisch. Ex Link) Fabaceae—Milk Vetch

From 1 kg of the root of milk vetch, cut to tiny pieces, an alcoholic extraction was made through 5 days. By cold distillation, alcohol was removed from the action. By further procedure, olygopeptides of milk vetch were frozen and lyophilized. In order to remove impurities contained by the plant extract, lyophilized milk vetch extract was applied on the column Sephadex G-25. Protein components were eluted from the column by the use of Tris-HCl buffer as the fraction 11. The absorption of protein was measured at 280 nm. Collected fractions from 1 ml each were submitted to the dialysis and lyophilized. The qualitative system of amino acids was determined on a thin layer of cellulose (Merck), in the mixture of the solvent: n-butanol:acetone acetic acid:water.

WORKING EXAMPLE 8

Isolation of Proteins of Balm

*Melissa Officinalis* L.—Balm

From 1 kg of the stalk and leaves of balm, cut to tiny pieces, an alcoholic extraction was made through 5 days. By cold distillation, alcohol was removed from the extraction. By further procedure, olygopeptides of balm were frozen and lyophilized. In order to remove impurities contained by the plant extract, lyophilized balm extract was applied on the column Sephadex G-25. Protein components were eluted from the column by the use of Tris-HCl buffer as the fraction 10. The absorption of protein was measured at 280 nm. Collected fractions from 1 ml each were submitted to the dialysis and lyophilized. The qualitative system of amino acids was determined on a thin layer of cellulose (Merck), in the mixture of the solvent: n-butanol:acetone acetic acid:water.

WORKING EXAMPLE 9

Isolation of Proteins of Hop

*Humulus Lupulus* L.—Hop

From 1 kg of the cones of hop, cut to tiny pieces, an alcoholic extraction was made through 5 days. By cold distillation, alcohol was removed from the extraction. By further procedure, olygopeptides of hop were frozen and lyophilized. In order to remove impurities contained by the plant extract, lyophilized hop extract was applied on the column Sephadex G-25. Protein components were eluted from the column by the use of Tris-HCl buffer as the fraction 12. The absorption of protein was measured at 280 nm. Collected fractions from 1 ml each were submitted to the dialysis and lyophilized. The qualitative system of amino acids was determined on a thin layer of cellulose (Merck), in the mixture of the solvent: n-butanol:acetone acetic acid:water.

Preparation of Vitamins

WORKING EXAMPLE 10

Preparation of B Complex

As the basic source of vitamins of the B complex was used an inactive preparation of yeasts rich in proteins, hydrocarbons, lipids, minerals, vitamins and essential amino acids. This preparation was used as the basic source of the B complex vitamins in the MPP.

WORKING EXAMPLE 11

Preparation of MPP

The MPP is prepared by mixing of the calcium form of the artificial zeolite, proteins of: nettle, milk vetch, balm and hop and the B-complex vitamins.

The MPP prepared in that way contains: 10 to 50% (m/m) of the calcium form of the zeolite.

($CaO \cdot Al_2O_3 \cdot ySiO_2 \cdot z'H_2O$), 0.5 to 20% (m/m) of the protein of the milk vetch root, 0.5 to 20% (m/m) of the protein of balm, 0.5 to 20% (m/m) of the protein of hop, 0.5 to 17.5% (m/m) of the protein of nettle and 0.5 to 12.5% (m/m) of B-complex.

WORKING EXAMPLE 12

Experimental Diabetes

Tests were made on two models of experimental diabetes.

Experimental diabetes was caused by alloxan in CBA mice, in the dose of 75 mg/kg of body weight. After the appearance of the symptoms of diabetes, 3 mice were kept in each cage.

NOD mice, which developed all the symptoms of diabetes, were taken in the experiment.

In pharmalogical tests, the mineral-herbal preparation was admixed to the standard food for laboratory mice.

This invention will now be shown with particular examples showing that, in case of diabetes, a syndrome is in question, and that for a successful treatment of Type I or II Diabetes, it is not sufficient to apply the known medicine which has only the characteristic of a strong hypoglycemic effectiveness, but that the mineral-herbal preparation from the invention should be applied which helps the disturbed metabolism in its entirety.

WORKING EXAMPLE 13

Determining of the Level of Apoptosis

The level of apoptosis was determined after cutting of the sample of the nerve in cryostat. On the cut samples of 4 µm, propidium iodine was added and the sample was analyzed under a fluorescent microscope.

WORKING EXAMPLE 14

Presence of IgG on Nerves

The presence of IgG on nerves was ascertained by colouring of nerves with peroxidase antiperoxidase and the analyzed under a microscope.

WORKING EXAMPLE 15

Diabetic animals which were receiving the MPP with the composition of minerals from 0.5 to 10 mg, proteins of milk vetch from 0.1 to 2 mg, proteins of nettle 0.1 do 1.5 mg, proteins of balm 0.1 to 2.0 mg, proteins of hop 0.1 to 2.0 mg, B1 vitamin from 0.5 to 10 µg, B2 from 2 to 10 µg, B6 from 0.5 to 1.25 µg, B12 from 0.3 to 1 µg, with all the symptoms of diabetes, with over 19.0 mmol/L of glucose in blood. Mice were placed in metabolic cages and, during 6 days, the quantity of water drunk, the quantity of food eaten, of urine and feces excreted were measured. During the first three days of the application of the MPP, the animals did not show a reduction of the symptoms of diabetes. The same was repeated in the next three days. The concentration of glucose in blood was above 16 mmol/L, and the animals drank over 25 ml of water daily. Further therapy had a positive effect on symptoms of diabetes in CBA and NOD mice. During the test, the mice were moderately active.

WORKING EXAMPLE 16

Diabetic animals which were receiving the MPP with the composition of minerals from 10 to 50 mg, proteins of milk vetch from 1 to 10 mg, proteins of nettle from 1 do 12 mg, proteins of balm 0 to 10 mg, proteins of hop 0 to 10 mg, B1 vitamin of 25 µg, B2 of 18 µg, B6 of 2.5 µg, B12 of 0.7 µg, with all the symptoms of diabetes, with over 14.5 mmol/L of glucose in blood. Mice were placed in metabolic cages and, during 6 days, the quantity of water drunk, the quantity of food eaten, of urine and feces excreted were measured. During the first three days of the application of the MPP, the animals considerably reduced the symptoms of diabetes. The same was repeated in the next three days, so that the volume of water drank and urine excreted was reduced by 60%. In the test of the effectiveness of the MPP on the concentration of glucose in the peripheral blood of diabetic mice, the preparation showed a hypoglycemic effect. Besides, the curve of the assimilation of glucose was considerably more favourable in relation to untreated control groups, which is valid both for CBA diabetic mice, and for NOD diabetic mice. During the further therapy, through 6 months, symptoms of diabetes were not completely removed, but they were considerably reduced. It should be particularly pointed out here that, beside the reduction of the concentration of glucose in blood, a considerable reduction of late complications of diabetes, e.g.: neuropathies, arose. During the tests, the mice were moderately active.

WORKING EXAMPLE 17

Diabetic animals which were receiving the MPP with the composition of minerals from 50 to 500 mg, proteins of milk vetch from 10 to 100 mg, proteins of nettle from 10 do 87.5 mg, proteins of balm 0 to 100 mg, proteins of hop 0 to 100 mg, B1 vitamin from 0.5 to 10 µg, B2 from 2 to 10 µg, B6 from 0.5 to 1.25 µg, B12 from 0.3 to 1 µg, with all the symptoms of diabetes, with over 16 mmol/L of glucose in blood. Mice were placed in metabolic cages and, during 6 days, the quantity of water drunk, the quantity of food eaten, of urine and feces excreted were measured. During the first three days of the application of the MPP, the animals considerably reduced the symptoms of diabetes. The same was repeated in the next three days, so that the volume of water drank and urine excreted was reduced by 70%. In the test of the effectiveness of the MPP on the concentration of glucose in the peripheral blood of diabetic mice, the MPP showed a hypoglycemic effect. However, the test of burdening with glucose did not show a positive effect of the preparation and the curve of the assimilation of glucose was not considerably more favourable in relation to unrelated control groups, which is valid both for CBA diabetic mice, and for NOD diabetic mice. During the further therapy, through 6 months, symptoms of diabetes were not completely removed, but they were considerably reduced. It should be particularly pointed out here that, for the purpose of reduction of the level of glucose, a considerable moves occurred, besides, the symptoms of diabetes were considerably reduced. During the test, the mice were moderately active.

Pharmacological Data

The effectiveness of the MPP on the concentration of glucose in blood was tested on control and diabetic CBA and NOD mice. The results were compared with the control group of diabetic CBA mice which were not receiving the MPP.

The animals were receiving the MPP by a probe during 14 days. On the 14$^{th}$ day, the zero blood sample (25 µl.) was taken from the tail vein. Firstly, the mice were submitted to testing of the effectiveness of the MPP, the mineral preparation (Working Example 1 to 3), secondly, of the effect of the mineral preparation plus plant proteins (Working Example 4 to 15).

Figure 6:
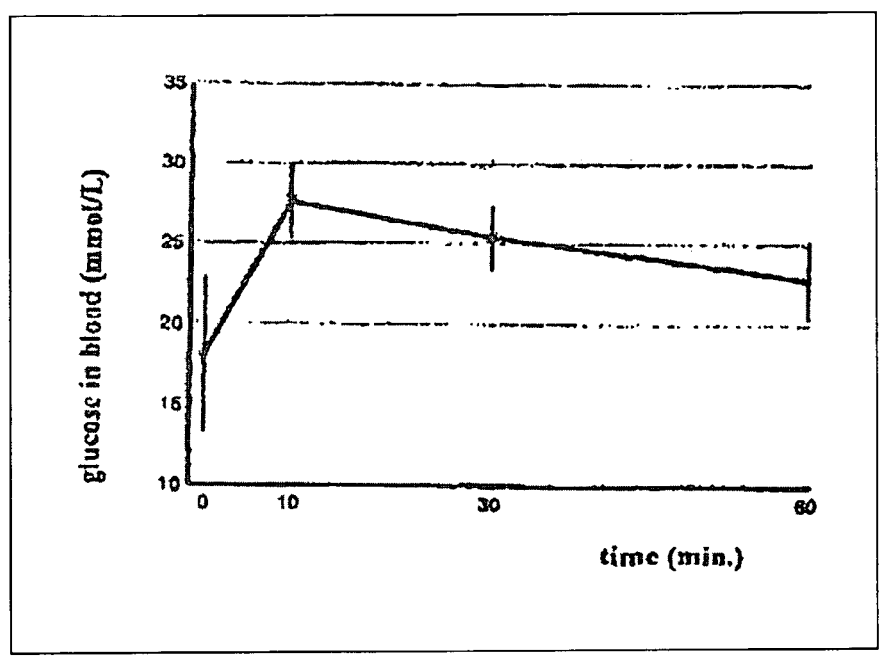
FIG. 6 is a chart showing the curve of the assimilation of glucose in diabetic CBA mice which were receiving the mineral part of MPP.
Figure 7:
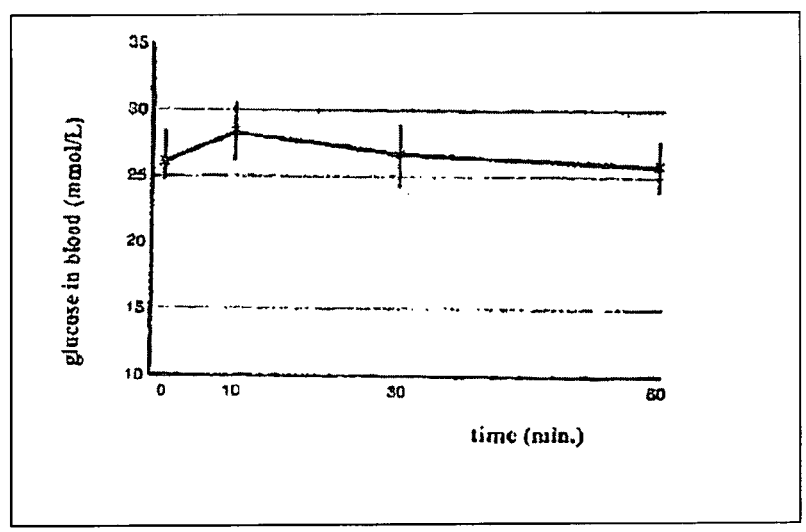
FIG. 7 is a chart showing the curve of the assimilation of glucose in diabetic NOD mice which were receiving the mineral pan of MPP

The results of burdening with glucose were presented in FIGS. 6 and 7.

The concentration of glucose in the blood of diabetic CBA mice (10 mice per group) which were not receiving the mineral part of the MPP averagely amounted to 19.8±3.2 mmol/L (FIG. 6). After 10, i.e. 30 minutes from the initiation of glucose (1 g/kg of body weight), the concentration of glucose in the peripheral blood of diabetic mice was strongly increased in value above 30 mmol/L. During the next half an hour, the concentration of glucose stated to be decreased, but after an hour's time, it did not reach the beginning values of the concentration of glucose in blood (FIG. 6).

In the group of diabetic mice which were receiving the mineral preparation MPP, the concentration of glucose in blood after initiating of glucose per os was strongly increased from 18 mmol/L to 27 mmol/L after 10 minutes. During the next 50 minutes, the concentration of glucose in the peripheral blood of diabetic mice was continuously decreasing (FIG. 6).

In the group of diabetic NOD mice, the test of burdening with glucose showed that the concentration of glucose in blood returned to the beginning values after 60 min. It can be concluded that the diabetic NOD mice which were receiving the mineral part of the MPP by probe assimilate the introduced glucose much better (FIG. 7). The mineral MPP preparation did not show a direct hypoglycemic effect.

Figure 8:
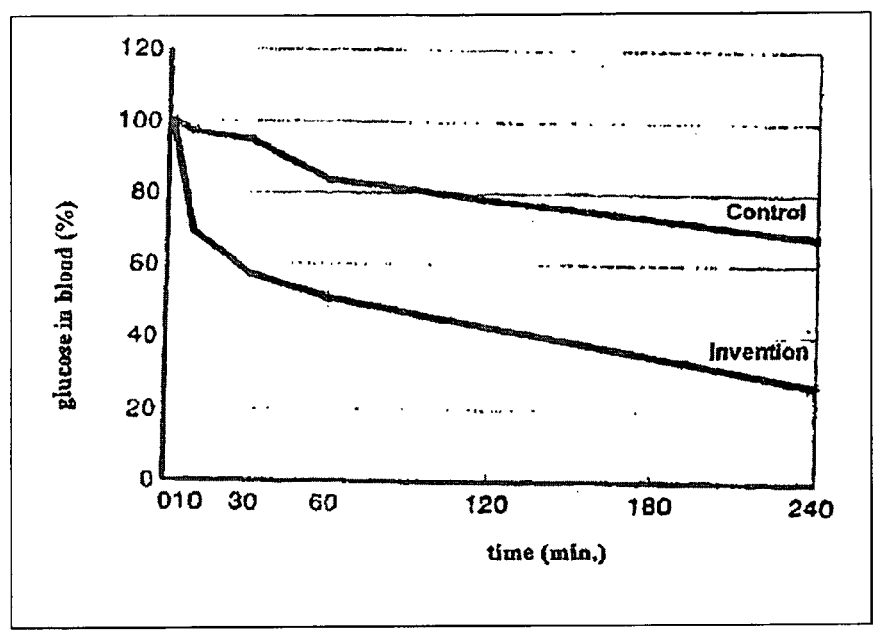
FIG. 8 is a chart showing the concentration of glucose in the blood of control diabetic mice (1) and diabetic mice treated with MPP (Working Example 16)

But, if diabetic mice were receiving MPP for 14 days, the concentration of glucose in the blood of those mice is presented in FIG. 8. Before probing with MPP, a sample of blood was taken and the zero value of the concentration of glucose was determined. During the next 4 hours of probing, in certain periods of time, a sample of their blood was taken, the concentration of glucose in diabetic mice was continuously falling and, after 4 hours, it amounted to only about 20% of the beginning value (FIG. 8). The mineral protein preparation according to the Working Example 16 showed a strong hypoglycemic effect during 4 hours of testing.

In diabetic mice which were receiving the MPP during 14 days (according to Working Example 17), the concentration of glucose in blood during four hours after introducing of the MPP was not changing in relation to control values. (FIG. 9).

Figure 10:
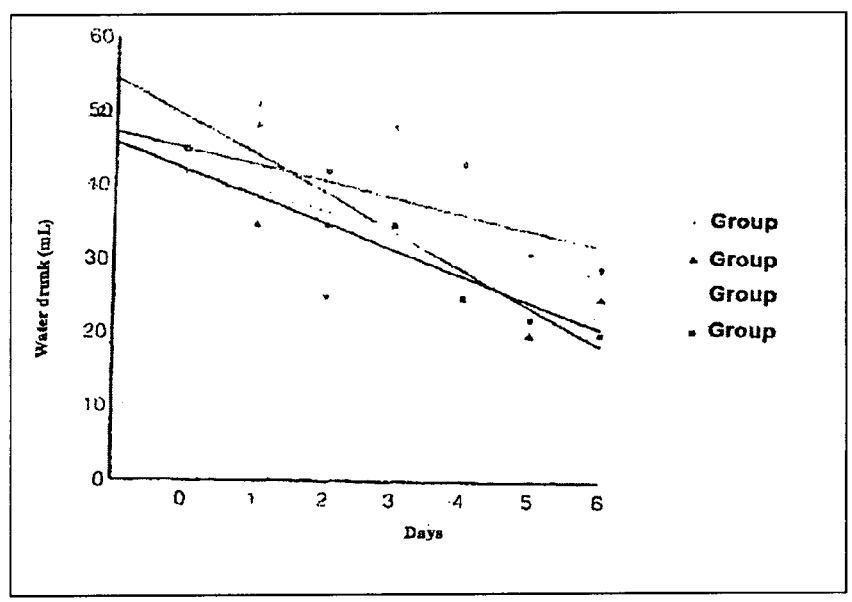
FIG. 10 is a chart showing the quantity of water drunk during 6 days of application of MPP (3 mice per group).

Diabetic CBA mice which were receiving MPP during 6 days considerably reduced the volume of the drunk water (p>0.001) (FIG. 10).

Figure 11:
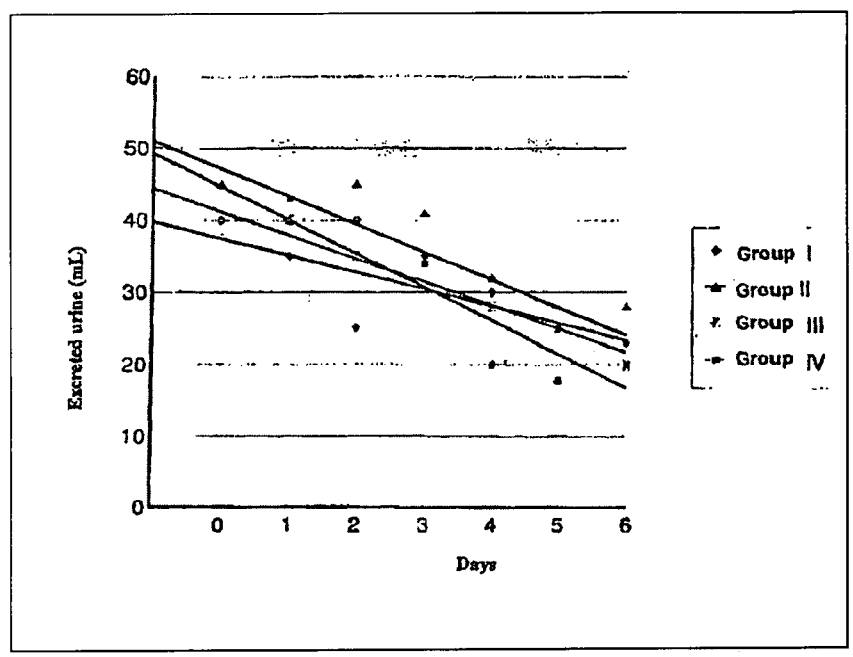
FIG. 11 is a chart showing the volume of excreted urine in diabetic mice which were receiving MPP (3 mice per group) or 6 days.

Diabetic CBA mice which were receiving MPP during 6 days considerably reduced the volume of the secreted urine (p>0.001) (FIG. 11).

During 6 months, mice were daily together with the MPP food. From Table 1, it is evident that the MPP has not shown a harmful effect because the body weight of the controlled, healthy mice was not being decreased, but it was increased during the experiment. Thus, the body weight was averagely increased from the beginning 25 grams to 39 grams.

But in the group of diabetic CBA mice, there was no increase of the body weights and it was averagely around 26 grams (Table 1). During the whole experiment, there was no increase of the body weight from the beginning values (Table 1), which is a usual occurrence in diabetes.

TABLE 1

The body weights of control and diabetic CBA mice which were receiving the MPP.

| Groups | Months | | | | | | |
|---|---|---|---|---|---|---|---|
| | 0 | 1 | 2 | 3 | 4 | 5 | 6 |
| Control | 24.3 ± 1.3 | 26.9 ± 2.1 | 29.7 ± 2.3 | 32.5 ± 2.8 | 33.6 ± 2.5 | 36.3 ± 2.2 | 39.3 ± 2.8 |
| Diabetic CBA | 27.7 ± 2.2 | 26.1 ± 1.2 | 26.2 ± 3.2 | 25.9 ± 3.7 | 25.7 ± 3.3 | 26.6 ± 2.8 | 26.5 ± 2.2 |

During the experiment, a decrease of the body weight was noticed in the group of diabetic NOD mice (Table 2).

In the beginning of the experiment, the body weight was about 35 grams, while mice were averagely weighing 30 grams (Table 2).

In the group of control, non-diabetic NOD mice, the body weight during the experiment was continuously increasing (Table 2).

Figure 12:
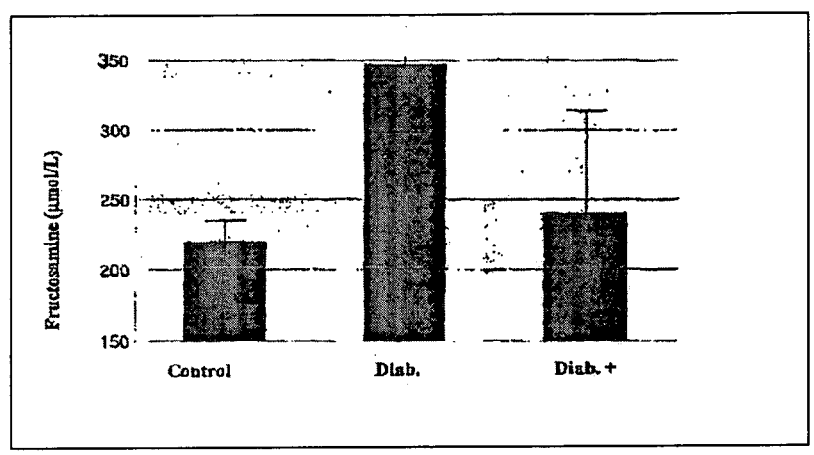
FIG. 12 is a chart showing the concentration of fructosamine in the serum of control (Control), diabetic (Diab. Groups), and diabetic mice treated with MPP (Diab.T) according to Working Example 16.

The concentration of fructosamine in the serum of diabetic NOD mice was determined for the purpose of monitoring the efficiency of the treatment of diabetes with the MPP. The results showed that the concentration of fructosamine in the control group of NOD mice amounts to 219 µmol/L. In the serum of diabetic NOD mice, the concentration of fructosamine is significantly increased. FIG. 12 (p<0.001). In the group of diabetic NOD mice treated with MPP, the measured concentration of fructosamine amounted to averagely 240 µmol/L, which is considerably lower in relation to the diabetic group (p<0.001) (FIG. 12).

In the cytosol of the liver of experimental groups, the effect of the mineral-plant preparation on the catalytic concentration of glutation S-transferase (GST) was determined.

GST is an enzyme of Phase II of metabolizing of xenobiotics and it participates in their detoxication and thus protects the station from the toxic effect of electrophilic substances. It catalyzes the reaction of conjugation of glutations with a large number of electrophilic components arisen in the cell.

Figure 13:
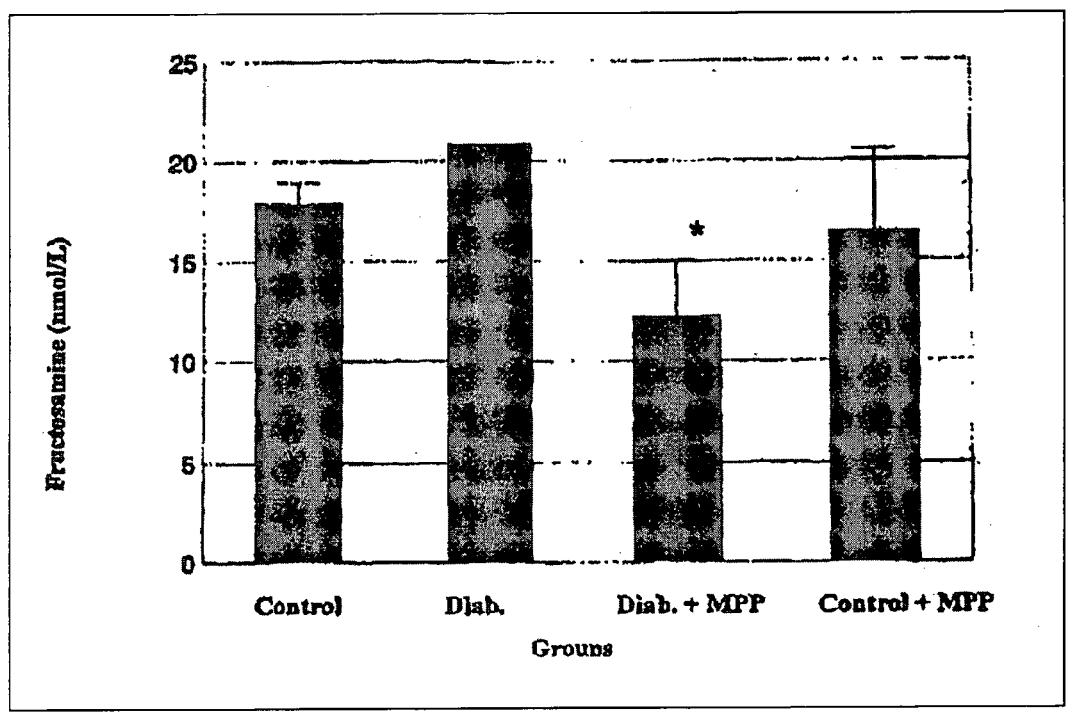
FIG. 13 is a chart showing the catalytic concentration of GST in the group of healthy, control and diabetic CBA mice treated with MPP (Diab.+MPP) (According to the Working Example 16.

The catalytic concentration of GST in the group of healthy, control and diabetic CBA mice amounted averagely to 17.19 nmol/min/mg (FIG. 13). In the group of healthy CBA mice treated with MPP, the catalytic concentration of GST amounted averagely to 16.42 nmol/min/mg. A considerable increase of the catalytic concentration of GST amounted averagely to 16.42 nmol/min/mg. A considerable increase of the catalytic concentration of GST arose in the group of diabetic CBA mice (p>0.05). After the six-month treatment of diabetic CBA mice with MPP, a considerable decrease of the catalytic concentration of GST in the liver occurred to averagely 12.23 nmol/min/mg, which is at the level of significance of p>0.01 a considerable difference in comparison with the diabetic group (FIG. 13).

During 6 months of testing of the effect of the MPP on the diabetic condition, the level of the concentration of calcium ions ($Ca^{2+}$) in the serum of control and diabetic mice was monitored (Table 3).

The concentration of ($Ca^{2+}$) ions during 6 months was not changed in the blood of diabetic CBA mice which were receiving the MPP daily (according to the Working Example 16). But in the group or diabetic CBA mice, a significant decrease in the concentrations of ($Ca^{2+}$) ions in the serum arose (p>0.05) after 6 months of the duration of the disease. Similar results were shown by mice with the spontaneous diabetes (Table 4). The concentration of ($Ca^{2+}$) ions was not changed in the group of diabetic NOD mice which were receiving the MPP daily. A considerable reduction of the concentration of calcium ions was measured in the group of diabetic NOD mice which were not receiving the MPP (p>0.005) (Table 4).

TABLE 2

The body weights of control and diabetic NOD mice which were receiving the MPP.

| Groups | Months | | | | | | |
|---|---|---|---|---|---|---|---|
| | 0 | 1 | 2 | 3 | 4 | 5 | 6 |
| NOD | 34.3 ± 3.8 | 33.7 ± 3.3 | 31.1 ± 4.1 | 30.5 ± 4.1 | 31.2 ± 4.4 | 30.9 ± 3.6 | 30.5 ± 3.2 |
| NOD non-diabetic | 30.4 ± 2.6 | 32.8 ± 3.4 | 35.6 ± 1.0 | 36.5 ± 2.3 | 37.8 ± 2.3 | 38.1 ± 2.6 | 39.4 ± 3.4 |

TABLE 3

Concentration of $Ca^{2+}$ in the serum of control and diabetic CBA mice which were receiving the MPP during 180 days.

| Groups | Days | | |
|---|---|---|---|
| | 7 | 90 | 180 |
| Diabetes | 2.2 ± 0.05 | 2.0 ± 0.06 | 1.92 ± 0.12* |
| Diabetes + MPP | 2.17 ± 0.03 | 2.19 ± 0.05 | 2.23 ± 0.2 |

TABLE 4

Concentration of $Ca^{2+}$ in the serum of control and diabetic CBA mice which were receiving the MPP during 180 days.

| Groups | Days | | |
|---|---|---|---|
| | 7 | 90 | 180 |
| NOD | 2.2 ± 0.08 | 2.01 ± 0.08 | 1.90 ± 0.04* |
| NOD + MPP | 2.2 ± 0.09 | 2.15 ± 0.03 | 2.16 ± 0.07 |

Animals form particular groups were sacrificed after 7, 90, that is 180 days. By patho-histological treatment, the level of neuropathy of the digestive tract (Tables 5 and 6) was ascertained. After 180 days, diabetic CBA mice which were not receiving the MPP, developed diabetic neuropathy in 100% of cases. However, in diabetic CBA mice which were receiving the MPP each day, the diabetic neuropathy was not observed (Table 5).

TABLE 5

Presence of neuropathy of the gastro-intestinal tract in diabetic CBA mice during 180 days of the duration of the experiment.

| Groups | Days | | |
|---|---|---|---|
| | 7 | 90 | 180 |
| Diabetes | − | + | +++ |
| Diabetes + MPP | − | + | + |

The same experiment was also done with diabetic NOD mice. Diabetic NOD mice develop diabetic neuropathy in 100% of cases during 6 months (Table 6). Diabetic NOD mice, which were receiving the MPP during 180 days each day did not develop diabetic neuropathy (Table 7).

TABLE 6

Presence of neuropathy of the gastro-intestinal tract in diabetic NOD mice during 180 days of the duration of the experiment.

| Groups | Days | | |
|---|---|---|---|
| | 7 | 90 | 180 |
| NOD | + | ++ | +++ |
| NOD + MPP | + | + | + |

In order to check the extent of the damage of nerves, i.e. to examine the presence of apoptotic bodies, on the day of sacrificing, samples of *n. ischiadicus* were taken from mice. The obtained results show that long-term diabetes has a considerable effect on the increase of the number of apoptotic bodies. In the group of diabetic mice, the number of apoptotic bodies was about 67% (Table 7). In controls (healthy mice), the number of apoptotic bodies was about 9%. Diabetic mice treated with the MPP did not show a considerable increase of the number of apoptotic bodies in *n. ischiadicus* (16%)(Table 7).

Figure 14:
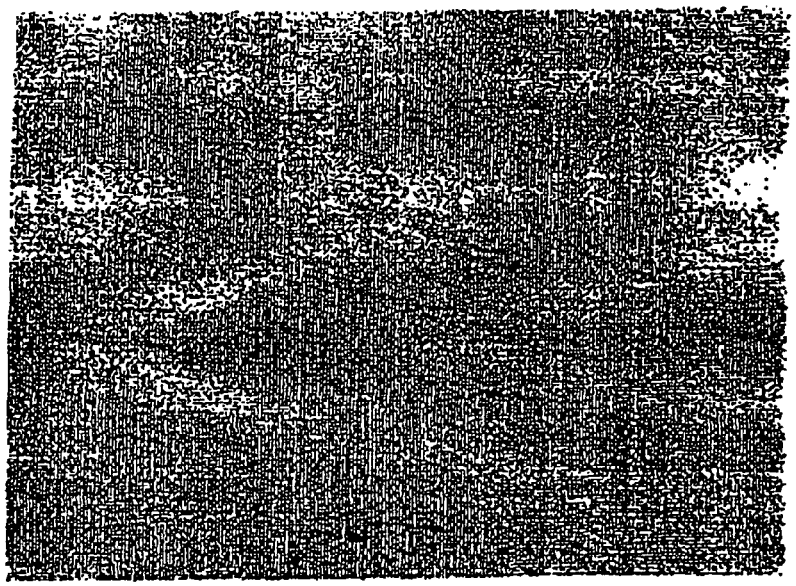
FIG. 14 depicts a cross-section through *n. ischiadicus* of diabetic mice after 180 days of the duration of the disease.
Figure 15:
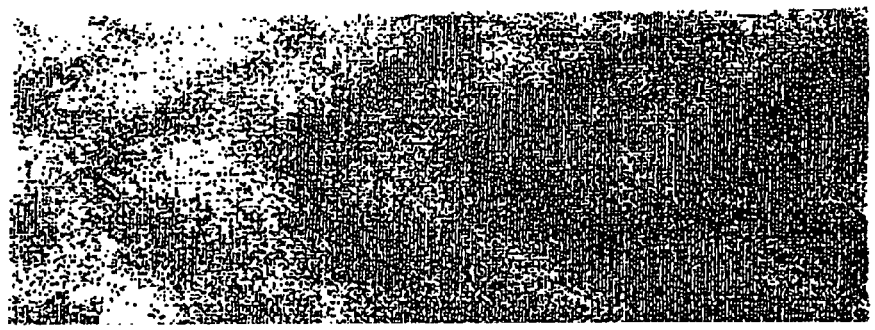
FIG. 15 depicts a cross-section through *n. ischiadicus* of diabetic mice treated with MPP after 180 days of the duration of the disease.

By peroxidase antiperoxidase colouring, the presence of antibodies (IgG) on *nervus ischiadicus* was tested. Diabetic mice which developed all the symptoms of diabetic neuropathy during the experiment showed a strong presence of IgG in *n. ischiadicus* (FIG. 14). Contrary to that, mice which were receiving the MPP for 6 months did not have autoantibodies on nerve fibres of *n. ischiadicus* (FIG. 15).

The percentage of apoptotic bodies is statistically considerably smaller in the group of mice (CBA and NOD) treated by the MPP (Tables 7 and 8). Further, after colouring with anti IgG conjugated with peroxidase antiperoxidase, the percentage of positive neurons in the group of mice treated by the MPP was between 6 and 9% (Tables 7 and 8).

TABLE 7

Percentage of apoptotic bodies, and the percentage of IgG positive nerve fibres in CBA mice after 6 months (180 days) of testing.

| Groups | Days | |
|---|---|---|
| | Apoptosis (%) | IgG (%) |
| Diabetes | 67 | 86 |
| Diabetes + MPP | 16 | 9 |

TABLE 8

Percentage of apoptotic bodies, and the percentage of IgG positive nerve fibres in NOD mice after 6 months (180 days) of testing.

| Groups | Days | |
|---|---|---|
| | Apoptosis (%) | IgG (%) |
| NOD | 78 | 91 |
| NOD + MPP | 12 | 6 |

No harmful toxic effects were ascertained if the animals were receiving the MPP during 6 months.

CONCLUSION

Since neuropathy is a late complication often present in diabetes, it was necessary to find the additional "means" to the therapy which will make the overall state of the patient considerably easier. For that purpose, the technical problem which was originally set before the inventor and finally successfully resolved resulted in the current invention of the mineral-protein preparation against neuropathies in diabetes with the following characteristics:

1) it reduces the concentration of glucose by its absorption on the MPP, which is evidenced by the figures showing the assimilation of glucose,
2) it stops the process of depositing of $Ca^{2+}$ ions into nerve cells,
3) it reduces the process of apoptosis in nerve cells stimulated by depositing of $Ca^{2+}$ ions,
4) the process of phagocytosis of apoptotic bodies is absent,
5) it stops the process of creating immunoglobulin on myelin fibres of the nerve membrane,
6) it reduces the depositing of immunoglobulin on nerve fibres,
7) it reduces the immunological destruction of nerve fibres mediated by the complement,
8) the pain caused by diabetic neuropathy is absent,
9) it contains the necessary active substances for elimination of neurotic digestive troubles,
10) it contains the necessary active substances for elimination of neurotic heart troubles,
11) it contains the necessary active substances for elimination of harmful radicals,
12) it contains the necessary B complex vitamins of natural origin,
13) mineral particles do not pass through villi,
14) mineral particles do not pass through the blood vessel barrier,
15) mineral particles do not pass through the intestine blood barrier,
16) the nature of the material is a strong ionic exchange,
17) it is suitable for oral administration and it had no harmful side effects during testing,
18) no noticeable harmful side effects appear even with large daily doses, and in case of a long-term use,
19) it is not harmful in case of its long-term use.

Working examples are given only as an illustration and they do not represent a limitation of the MPP, the range of which is determined by the contents of patent applications.

The invention claimed is:

1. A mineral-protein preparation, comprising
synthetic Ca-zeolite,
protein extract of nettle,
protein extract of milk vetch,
protein extract of balm,
protein extract of hop cones, and
a source of B-complex vitamins.

2. The mineral-protein preparation according to claim 1 comprising

| | |
|---|---|
| synthetic Ca-zeolite | 10–50 m/m % |
| protein extract of nettle | 0.5–17.5 m/m % |
| protein extract of milk vetch | 0.5–20 m/m % |
| protein extract of balm | 0.5–20 m/m % |
| protein extract of hop cones | 0.5–20 m/m % |
| a source of B-complex vitamins | 0.5–12.5 m/m %. |

3. The mineral-protein preparation according to claim 2 comprising

| | |
|---|---|
| synthetic Ca-zeolite | 40 m/m % |
| protein extract of nettle | 15 m/m % |
| protein extract of milk vetch | 15 m/m % |
| protein extract of balm | 10 m/m % |
| protein extract of hop cones | 10 m/m % |
| a source of B-complex vitamins | 10 m/m %. |

4. The mineral-protein preparation of claim 2 wherein the synthetic zeolite was prepared by crystallization of an aluminosilicate hydrogel obtained by mixing an alkaline solution of sodium aluminate and an alkaline solution of sodium silicate after which ionic exchange of the synthetic zeolite was carried out, during which $Na^+$ ions were replaced with $Ca^{2+}$ ions.

5. The mineral-protein preparation of claim 4, wherein the sodium content of the synthetic zeolite is reduced by procedures of ionic exchange to 7.2% from 17.2% of $Na^+$ ions, calculated as $Na_2O$ and the calcium content is increased to 15.6% from 6.5% $Ca^{2+}$ ions, calculated as CaO.

6. The mineral-protein preparation according to claim 5, comprising

| | |
|---|---|
| 6.5–15.6% | CaO, |
| 11.8–28.4% | $Al_2SO_3$, |
| 33.5–69.3% | $SiO_2$, and |
| 12.5–22.6% | $H_2O$. |

7. The mineral-protein preparation according to claim 6 wherein the calcium synthetic zeolite is 95–100% crystalline and without admixtures of other non-zeolite crystalline phases.

8. The mineral-protein preparation according to claim 6, wherein the synthetic zeolite is present in particles ranging in size from 0.5 to 20 micrometers.

9. The mineral-protein preparation according to claim 8, wherein the specific surface of the synthetic zeolite particles is from 0.15 to 6 $m^2/g$.

10. The mineral-protein preparation according to claim 2 wherein the protein extracts are obtained by the purification of the alcoholic extract of each on Sphadex G-25.

11. The mineral-protein preparation according to claim 2 wherein the source of the B-complex vitamins contained in the preparation is inactive yeast.

12. The mineral-protein preparation according to claim 2 wherein the inactive yeast is *Saccharomices* Sp.

13. A medicament comprising the preparation of claim 1 and physiologically acceptable auxiliary substances.

14. The medicament of claim 13 formulated for peroral administration.

15. The medicament of claim 14 in tablet form.

16. A method of treating a diabetic mammal to reduce one or more of the concentration of GUK, fluid intake, the process of apoptosis in nerve cells, the process of creating of IgG on myelin fibres of nerve membranes or the process of phagocytosis of apoptotic bodies comprising administering to a patient in need thereof a therapeutically effective amount of the medicament of claim 13.

17. A method for the treatment of diabetic neuropathies comprising administering to a patient in need thereof a therapeutically effective amount of the medicament of claim 13.

18. A method of
reducing, in a diabetic mammal, one or more of
the concentration of glucose in the blood,
the amount of fructosamine in the blood,
the concentration of GST in the liver or
minimizing in a diabetic mammal one or more of
the presence of apoprotic bodies or
diabetic neuropathy of the digestive tract, or
maintaining the level of $Ca^{2+}$ ions in the serum of a diabetic mammal,
comprising administering to a patient in need thereof a therapeutically effective amount of the medicament of claim 13.

* * * * *